United States Patent [19]

Bazinet et al.

[11] Patent Number: 4,970,299

[45] Date of Patent: Nov. 13, 1990

[54] MONOCLONAL ANTIBODIES SELECTIVE FOR PROSTATE CANCER

[75] Inventors: Michel Bazinet; Richard J. Cote; Lloyd J. Old, all of New York, N.Y.

[73] Assignee: Sloan-Kettering Institute for Cancer Research, New York, N.Y.

[21] Appl. No.: 881,630

[22] Filed: Jul. 3, 1986

[51] Int. Cl.$^5$ .......................... C07K 15/28; C12N 5/12
[52] U.S. Cl. .................................. 530/387; 530/391; 530/809; 435/240.27; 435/70.2; 435/70.21; 435/172.2; 435/7; 435/188; 435/810; 436/548; 935/100; 935/104; 935/107; 935/108; 935/110; 424/85.8; 424/85.91
[58] Field of Search ............... 530/387, 388, 391, 809; 435/240.27, 68, 172.2, 7, 188, 810, 70.2, 70.21; 436/548; 935/100, 104, 107, 108, 110; 424/85.8, 85.91

[56] References Cited

U.S. PATENT DOCUMENTS

| | | |
|---|---|---|
| 4,361,549 | 11/1982 | Kung . |
| 4,361,550 | 11/1982 | Kung . |
| 4,363,799 | 12/1982 | Kung . |
| 4,364,932 | 12/1982 | Kung . |
| 4,364,933 | 12/1982 | Kung . |
| 4,364,934 | 12/1982 | Kung . |
| 4,364,935 | 12/1982 | Kung . |
| 4,364,936 | 12/1982 | Kung . |
| 4,364,937 | 12/1982 | Kung . |
| 4,650,756 | 3/1987 | Old et al. . |

FOREIGN PATENT DOCUMENTS

2139645 11/1984 United Kingdom .

OTHER PUBLICATIONS

Starling, J. J. et al., *Cancer Res.*, vol. 46, pp. 367–374, (1986).
Eisinger, M. and Marko, O., *Proc. Natl. Acad. Sci. USA*, vol. 79, pp. 2018–2022 (1982).
Old, L. J., *Cancer Res.*, vol. 41, pp. 361–375 (1981).
Dippold, W. G. et al., *Proc. Natl. Acad. Sci. USA*, vol. 77, pp. 6114–6118 (1980).
Bazinet, M. et al., "Specificity Analysis of Mouse Monoclonal Antibodies Reactive with Prostate Cancer," *J. Urology* ±(4 Parts): 111A, 1986.
Finstad, C. L. et al., "Specificity Analysis of Mouse Monoclonal Antibodies Defining Cell Surface Antigens of Human Renal Cancer," *Proc. Nat'l Acad. Sci.* 82:2955–2959, May 1985.
Starling, J. J. et al., "Monoclonal Antibodies to Human Prostate and Bladder Tumor-Associated Antigens," *Canc. Res.* 42: 3084–3089, Aug. 1982.

*Primary Examiner*—Garnette D. Draper
*Assistant Examiner*—Paula Hutzell
*Attorney, Agent, or Firm*—John P. White

[57] ABSTRACT

Four monoclonal antibodies are found which selectively identify prostate cancer. These monoclonals are therefore useful in diagnosis, differential diagnosis and treatment of prostate cancer.

4 Claims, No Drawings

MONOCLONAL ANTIBODIES SELECTIVE FOR PROSTATE CANCER

The invention was made in part with government support under CA 08748 awarded by the National Cancer Institute. The government has certain rights in this invention.

The present invention relates to a method of using monoclonal antibodies and their antigenic specificities in identifying, characterizing, and determining a prognosis for human prostate cancers. This is a useful diagnostic tool in the detection, clinical prognosis and therapy of prostate cancer as well as in the the study of the nature of prostate cancer. Antigenic profiles offer insight into prognosis for prostate cancer types.

Red blood cells, immunofluorescent, radioactive or enzymatic tagging agents can be bound to the highly specific antibodies using normal procedures, such as those required for indexing methods. Cytotoxic or cytostatic agents can also be bound to the highly specific antibodies to produce so called "magic bullet" type therapeutic agents which selectively destroy the cells with which the specific antibody binds.

In 1975 Köhler and Milstein introduced a procedure for the production of monoclonal antibodies (mAbs) using hybrid cells (hybridomas) which allows the production of almost unlimited quantities of antibodies of precise and reproducible specificity. Conventional antisera, produced by immunizing animals with tumor cells or other antigens, contain a myriad of antibodies differing in their specificity and properties, whereas hybridomas produce a single antibody with uniform characteristics. The Kohler-Millstein procedure entails the fusion of spleen cells from an immunized animal with an immortal myeloma cell line. From the fused cells (hybridomas), clones are selected that produce antibody of the desired specificity. Each clone continues to produce only that one antibody. As hybridoma cells can be cultured indefinitely (or stored frozen in liquid nitrogen), a constant supply of antibody is assured.

Antibodies are proteins that have the ability to combine with and recognize other molecules known as antigens. Monoclonal antibodies are no different from other antibodies except that they are very uniform in their properties and recognize only one antigen or a portion of an antigen known as a determinant.

In the case of cells, the determinant recognized is an antigen on or in the cell which reacts with the antibody. It is through these cell antigens that a particular antibody recognizes, i.e. reacts with, a particular kind of cell. Thus the cell antigens are markers by which the cell is identified.

These antigenic markers may be used to observe the normal process of cell differentiation and to locate abnormalities within a given cell system. The process of differentiation is accompanied by changes in the cell surface antigenic phenotype, and antigens that distinguish cells belonging to distinct differentiation lineages, or distinguish cells at different phases in the same differentiation lineage, may be observed if the correct antibody is available. Initial recognition of differentiation antigens came about through analysis of surface antigens of T-cell leukemias of the mouse and the description of the TL, Thy-1, and Lyt series of antigens. (Old, Lloyd J., Cancer Research, 41, 361-375, February 1981). The analysis of these T-cell differentiation antigens has been greatly simplified by the availability of normal human and murine T cells and B cells and is relatively advanced. (See Pat. Nos. #4,361,549-550; #4,364,932-37 and #4,363,799 concerning mAb to Human T-cell antigens). Little is known about differentiation antigens displayed on normal and neoplastic cells belonging to other lineages, especially prostate.

This is due to the difficulty of obtaining a ready source of the appropriate normal or tumor cell type as well as to the vagaries of the art of monoclonal an&.ibodies. The preparation of hybrid cell lines can be successful or not depending on such experimental factors as nature of the innoculant, cell growth conditions, hybridization conditions etc. Thus it is not always possible to predict successful hybridoma preparation for one cell line although success may have been achieved with another cell line.

Progress in defining surface antigens on melanocytes was made possible by the recently discovered technique of culturing melanocytes from normal skin (Eisinger, et al., Proc. Nat'l. Acad. Sci. USA, 79 2018 (March 1982). This method provides a renewable source of proliferating cells for the analysis of melanocyte differentiation antigens.

Cell surface antigens of human malignant melanoma was identified by mouse monoclonal antibodies (mAbs) (Dippold et al. Proc. Natl. Acad. Sci. USA 77, 6114–6118 (1980)). Previous work on $S_{27}$ (a well-characterized mAb initially developed in our laboratory against renal cancer) in renal cancer is found in a co-pending patent application U.S.A. Ser. No. 277,814, Monoclonal Antibodies To Cell Surface Antigens of Human Renal Cancer, and Ser. No. 474,224 Monoclonal Antibodies to Human Renal Cancer Antigens and Method hereby incorporated by reference.

Co-pending U.S. Patent Application Ser. No. 297,814, filed Aug. 31, 1981, now U.S. Pat. No. 4,650,756, issued Mar. 17, 1987 of melanoma (Dippold, et al Proc. Natl. Acad. Sci. U.S.A. 77, 6114–6118 (1980)), describes a series of mouse Abs that defined 12 new systems of human cell surface antigens. Six of these had been identified as glycoproteins (gp95, gp150, gp160, gp120r, gp120nr, and gp115), three are heat-labile antigens that could not be immunoprecipitated from labeled cell extracts ($S_{25}$, $M_{19}$, and $R_8$), and three are heat-stable antigens, presumably glycolipids ($O_5$, $R_{24}$, and $V_1$).

Monoclonal antibody technology is being applied in many areas of oncology. Mouse monoclonal antibodies (mAb) are currenly being used in the immunohistological diagnosis and classification of tumors and in tumor localization and therapy.

Several laboratories have generated mAbs that recognize antigens associated with prostatic tissues, including several which appear to be prostate-specific. However, most of these antibodies react with antigens expressed by both benign and malignant prostatic tissues. In order to facilitate the diagnosis and further characterize the progression of this malignancy, it would be of interest to define markers which distinguish benign from malignant prostatic tissues.

We report here on the initial analysis and distribution of four mAbs reactive with prostate cancer.

Materials and Methods

Three mAbs — P25.15 (IgG$_1$), P25.48 (IgG$_3$) and P25.91 (IgG$_{2a}$) — were derived from a fusion using fresh prostate cancer (P251) as the immunogen. The mouse splenocytes were fused with the NS-1 mouse myeloma using standard Kohler-Milstein techniques. The initial screening of hybrid supernatants were performed on frozen sections of the tumor P25I using indirect immunofluorescence (IIF) by methods known in the art. Positive clones were subcloned three times by limiting dilution. Further analysis on different prostatic tissues was performed by IIF and/or indirect immunoperoxidase (IIP) staining of frozen tissue sections using the avidin-biotin immunoperoxidase system (Vector Laboratories). The analysis on non-prostatic tissues were performed exclusively by IIP.

S27 (IgG$_1$) is a well-characterized mAb initially developed in our laboratory against renal cancer that has been shown to react with prostate (Finstad et al. *Proc. Nat'l. Acad. Sci. U.S.A.* 1985; 82:2955). It has been shown to recognize adenosine deaminase-binding protein (gp120). SK-RC-7 is the immunogen cell line leading to mAb S27. TURP-27 (IgG$_3$) developed by Wright et al (*Cancer Res.* 1986; 46:367) detects an antigen expressed by benign and malignant prostatic epithelium but not by most normal tissues. Hybridoma culture supernatants of S27 and TURP-27 were used for IIF and IIP analysis as described above.

S27 has been deposited at the Sloan-Kettering Institute, 1275 York Avenue, New York, N.Y. 10021 and at the American Type Culture Collection (ATCC), 12301 Parklawn Drive, Rockville, Md. 20852 on Nov. 15, 1983, has the ATCC designation HB 8428 and is a deposit under the Budapest Treaty.

P25.48, P25.91 and P25.15 are on deposit at Sloan-Kettering and at the ATCC under the designations below.

(a) the hybridoma cell line designated P25.15 was deposited under American Type Culture Collection (ATCC) Accession No. HB9140 on July 3, 1986;

(b) the hybridoma cell line designated P25.91 was deposited under American Type Culture Collection (ATCC) Accession No. HB9120 on June 6, 1986; and (c) the hybridome cell line designated P25.48 was deposited under American Type Culture collection (ATCC) Accession No. HB9119 on June 6, 1986.

Each of these hybridoma cell lines has been deposited with the American Type Culture Collection (ATCC), 12301 Parklawn Drive, Rockville, Md. 120852 pursuant to and in satisfaction of the requirements of the Budapest Treaty on the International Recognition of Microorganisms for Purposes of Patent Procedure.

TABLE I

INDIRECT IMMUNOFLUORESCENCE AND IMMUNO-PEROXIDASE ANALYSIS OF FROZEN SECTIONS OF PROSTATIC TISSUES

| SPECIMENS | P25.48 IgG$_3$ | P25.91 IgG$_{2a}$ | P25.15 IgG$_1$ | S27 IgG$_1$ |
|---|---|---|---|---|
| NORMAL | | | | |
| P12I | — | — | — | + |
| P21I | — | — | + | ++[b] |
| BPH (Benign Prostatic Hyperplasia) | | | | |
| P6I | — | — | + | ++ |
| P11I | — | — | — | ++ |
| P14I | — | — | — | ++ |
| P15I | — | — | — | ++ |
| P18I | — | — | — | ++ |
| P19I | — | — | | |
| P26I | — | — | | |
| P34I | — | — | ++[b] | ++ |
| P39I | — | — | + | ++[b] |
| P67I | —[a] | — | | |
| P68I | — | — | | |
| P72I | —[a] | —[a] | | |
| P78I | — | — | | |
| CARCINOMA Well-Differentiated | | | | |
| P32I | — | — | ++ | ++[b] |
| P55I | | | | ++ |
| P83I | — | — | | |
| Moderately Well-Differentiated | | | | |
| P10I | — | — | — | ++ |
| P30I | ++ | ++ | ++ | ++[b] |
| P35I | — | — | ++ | ++[b] |
| P36I | — | — | — | ++[b] |
| P53I | ++[b] | ++[b] | ++[b] | — |
| P54I | ++[b] | ++[b] | ++ | ++[b] |
| Moderately to Poorly Differentiated | | | | |
| P25I | ++ | ++ | ++ | ++ |
| P44I | ++[b] | ++[b] | ++ | ++[b] |
| Poorly or Undifferentiated | | | | |
| P46I | + | + | + | ++[b] |
| P50I | — | — | — | — |
| P65I | ++ | + | — | — |

— NO REACTIVITY
+ WEAK REACTIVITY
++ STRONG REACTIVITY
[a]Epithelium negative but some glands contained positive secretions.
[b]Heterogenous reactivity.

TABLE II

INDIRECT IMMUNOPEROXIDASE ANALYSIS OF FROZEN SECTIONS OF NON PROSTATIC TISSUES

| | # | P25.48 IgG$_3$ | P25.91[a] IgG$_{2a}$ | # | P25.15 IgG$_1$ | S27 IgG$_1$ |
|---|---|---|---|---|---|---|
| NORMAL TISSUES | | | | | | |
| Lung | (3) | — | — | (2) | ½ | — |
| Bronchus | (1) | — | — | (1) | ++ | — |
| Liver | (2) | — | ½ | (1) | ++ | + |
| Stomach | (3) | — | — | (2) | — | —[c] |
| Jejunum | (1) | — | — | (1) | + | ++ |
| Colon | (3) | — | — | (2) | — | —[c] |
| Salivary | (2) | — | — | (1) | ++ | ++ |
| Pancreas | (2) | — | — | (2) | ++/+ | — |
| Thyroid | (1) | — | — | (1) | — | — |
| Adrenal | (2) | — | — | (1) | — | — |
| Kidney | (3) | — | ½[b] | (1) | — | ++ |
| Ureter | (1) | — | — | | | |
| Bladder | (1) | — | — | (1) | ++ | — |
| Seminal Vesicle | (2) | — | — | (2) | ½ | ½ |
| Vas Deferens | (1) | — | — | (1) | — | ++ |
| Testis | (1) | — | — | | | |
| Atrophic Ovary | (1) | — | — | | | |
| Fallopian Tube | (1) | — | — | | | |
| Uterine Cervix | (1) | —[c] | — | | | |
| Breast | (2) | ½[d] | ½[d] | | | |
| Skin | (1) | — | — | (1) | — | — |
| MALIGNANT TISSUES | | | | | | |
| Lung | (1) | — | — | | | |
| Breast | (3) | — | — | | | |
| Stomach | (1) | — | — | | | |
| Salivary | (1) | — | — | | | |
| Kidney | (1) | — | — | | | |
| Bladder | (1) | — | — | | | |
| Seminoma | (1) | — | — | | | |

TABLE II-continued
INDIRECT IMMUNOPEROXIDASE ANALYSIS OF FROZEN SECTIONS OF NON PROSTATIC TISSUES

|  | # | P25.48 IgG$_3$ | P25.91[a] IgG$_{2a}$ | # | P25.15 IgG$_1$ | S27 IgG$_1$ |
|---|---|---|---|---|---|---|
| Melanoma | (2) | — | — | | | |

− NO REACTIVITY
+ WEAK REACTIVITY
++ STRONG REACTIVITY
[a]Although clearly negative on epithelial cells, P25.91 is weakly reactive with the stroma in 60% of the specimens tested.
[b]Weak reactivity with the proximal tubule.
[c]Epithelium negative but stroma showed weak reactivity.
[d]Some ducts showed strong reactivity.

We see from Tables I and II that P25.48 and P25.91 appear to distinguish benign from malignant prostatic epithelium. They react with a subset of prostatic cancers (7/13) but do not react with benign prostatic epithelium (0/15).

The antigens recognized by P25.48 and P25.91 show a very restricted distribution on normal and malignant non-prostatic tissues (Table II).

P25.15 and S27 react with most benign and malignant prostatic tissues. The reactivity of S27 on malignant prostatic tissues is frequently heterogenous, although it is usually homogeneous on benign epithelium. S27 and P25.15 were found to react with a subset of normal tissues. They were found to react with most prostate tissues tested, including benign prostates and prostate cancers.

The antigens recognized by P25.15 and S27 show moderate degree of restriction for normal tissues.

These antibodies are therefore useful for the diagnosis, subclassification, imaging, and therapy of prostatic cancer.

For imaging the monoclonal antibody can be linked or bound to a radioactive or fluorescent substance. For diagnosis antigen-antibody complex can be detected or visualized by methods known in the (art such as mixed hemabsorption assay, rosetting, immunofluorescence and immunoperoxidase techniques etc.). For therapy, the monoclonal antibody can be linked to a radioactive label, a drug or therapeutic material, or a poison or cytotoxic agent to help kill the cancer cells bound by the monoclonal antibody.

What is claimed:
1. The monoclonal antibody P25.48.
2. The hybridoma cell ilne which produces the monoclonal antibody P25.48 (ATCC Accession No. HB 9119).
3. The monoclonal antibody P25.91.
4. The hybridoma cell line which produces the monoclonal antibody P25.91 (HB 9120).

* * * * *